(12) United States Patent
Ofer et al.

(10) Patent No.: US 10,056,164 B2
(45) Date of Patent: Aug. 21, 2018

(54) TRANSLATING X-RAY BEAM TRANSMISSION PROFILE SHAPER

(71) Applicant: KONINKLIJKE PHILIPS N.V., Eindhoven (NL)

(72) Inventors: Oren Ofer, Mitspe Aviv (IL); Oren Zarchin, Raanana (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/646,102

(22) PCT Filed: Nov. 18, 2013

(86) PCT No.: PCT/IB2013/060219
§ 371 (c)(1),
(2) Date: May 20, 2015

(87) PCT Pub. No.: WO2014/087283
PCT Pub. Date: Jun. 12, 2014

(65) Prior Publication Data
US 2015/0302946 A1    Oct. 22, 2015

Related U.S. Application Data

(60) Provisional application No. 61/732,516, filed on Dec. 3, 2012.

(51) Int. Cl.
*G21K 1/10* (2006.01)
*G21K 1/04* (2006.01)
(Continued)

(52) U.S. Cl.
CPC ............. *G21K 1/043* (2013.01); *A61B 6/06* (2013.01); *A61B 6/405* (2013.01); *A61B 6/4035* (2013.01); *G01N 23/04* (2013.01); *G21K 1/10* (2013.01)

(58) Field of Classification Search
CPC ........... G21K 1/10; G21K 1/025; G21K 1/04; G21K 1/02; G21K 1/043; A61B 6/4035
See application file for complete search history.

(56) References Cited

U.S. PATENT DOCUMENTS 3,852,603 A * 12/1974 Muehllehner ......... G01T 1/2985
250/363.04
3,988,585 A   10/1976 O'Neill et al.
(Continued)

FOREIGN PATENT DOCUMENTS

EP   0496438 A1   7/1992
JP   6-77705      11/1994
(Continued)

*Primary Examiner* — Brooke Purinton (57) ABSTRACT

An imaging system (300) includes a radiation source (308) that emits radiation that traverses in a direction of an examination region (306) during a scan and a detector array (316) located opposite the radiation source, across the examination region, which detects radiation traversing the examination region during the scan and produces a signal indicative thereof. A beamshaper (318), located between the radiation source and the examination region, defines a flux intensity profile of the radiation beam traversing the examination region. The beamshaper includes a plurality of x-ray attenuating elements(326), which attenuate x-rays incident thereon, interleaved with a plurality of material free regions, which pass x-ray unattenuated. A transmittance of the x-rays is greater nearer a center region of the beamshaper relative to ends regions of the beamshaper. A beamshaper mover (328) translates the beamshaper during at least one acquisition interval of the scan.

20 Claims, 8 Drawing Sheets (51) Int. Cl.
  *A61B 6/06* (2006.01)
  *A61B 6/00* (2006.01)
  *G01N 23/04* (2018.01)

(56) References Cited

U.S. PATENT DOCUMENTS

| | | | |
|---|---|---|---|
| 4,096,389 A | 6/1978 | Ashe et al. | |
| 4,288,695 A | 9/1981 | Walters et al. | |
| 4,541,107 A * | 9/1985 | Rossi | A61B 6/06 378/145 |
| 4,672,648 A | 6/1987 | Mattson et al. | |
| 4,914,685 A | 4/1990 | Yanome | |
| 4,953,192 A | 8/1990 | Plewes | |
| 5,332,908 A * | 7/1994 | Weidlich | A61N 5/1042 250/492.1 |
| 5,644,612 A * | 7/1997 | Moorman | A61B 6/06 378/146 |
| 6,088,427 A | 7/2000 | Pagano | |
| 6,353,227 B1 * | 3/2002 | Boxen | G21K 1/025 250/363.06 |
| 6,408,054 B1 | 6/2002 | Rahn et al. | |
| 7,082,189 B2 | 7/2006 | Yahata | |
| 2003/0198319 A1 | 10/2003 | Toth et al. | |
| 2006/0072705 A1 | 4/2006 | Munro | |
| 2007/0086576 A1 * | 4/2007 | Yang | A61B 6/06 378/152 |
| 2008/0037709 A1 * | 2/2008 | Yatsenko | G21K 1/10 378/145 |
| 2009/0074148 A1 * | 3/2009 | Echner | G21K 1/04 378/152 |
| 2009/0220046 A1 | 9/2009 | Ji | |
| 2010/0111261 A1 * | 5/2010 | Maack | H05G 1/02 378/150 |
| 2011/0013742 A1 * | 1/2011 | Zaiki | A61B 6/035 378/15 |
| 2011/0210256 A1 | 9/2011 | Mattson et al. | |
| 2012/0140885 A1 * | 6/2012 | Iwakiri | A61B 6/06 378/62 |
| 2012/0163554 A1 | 6/2012 | Tada | |
| 2014/0112431 A1 | 4/2014 | Mattson et al. | |

FOREIGN PATENT DOCUMENTS

| | | |
|---|---|---|
| JP | 2004049849 | 2/2004 |
| JP | 2005118382 A | 5/2005 |
| JP | 2009273745 | 11/2009 |
| WO | 2009017348 | 2/2009 |
| WO | 2013001386 | 1/2013 |
| WO | 2014087283 A1 | 6/2014 |
| WO | 2014087305 A1 | 6/2014 |

* cited by examiner

FIG. 16

TRANSLATING X-RAY BEAM TRANSMISSION PROFILE SHAPER

CROSS REFERENCE TO RELATED APPLICATIONS

This application is a national filing of PCT application Serial No. PCT/IB2013/060219, filed Nov. 18, 2013, publishied as WO 2014/087283 A1 on Jun. 12, 2014, which claims the benefit of U.S. provisional application Ser. No. 61/732,516 filed Dec. 3, 2012, which is incorporated herein by reference.

The following generally relates to translating an x-ray beamshaper, which includes attenuating and non-attenuating regions and which is configured to shape a transmission flux profile during at least one acquisition interval, and is described with particular application to computed tomography (CT); however, the following is also amenable to other imaging modalities such as x-ray.

A CT scanner includes an x-ray tube that emits radiation from a focal spot in a direction of an examination region. A source collimator is disposed between the focal spot and the examination region and collimates the emitted radiation to produce a beam having a pre-determined geometrical shape (e.g., fan, cone, etc.). The collimated beam traverses the examination region and a portion of an object or subject therein (which attenuates the beam as a function of the radiodensity of the object or subject) and illuminates a detector array disposed across the examination region, opposite the x-ray tube. The detector produces projection data indicative of the detected radiation. The projection data is reconstructed, generating volumetric image data indicative thereof The volumetric image data can be processed to generate one or more images indicative thereof.

Figure 1:
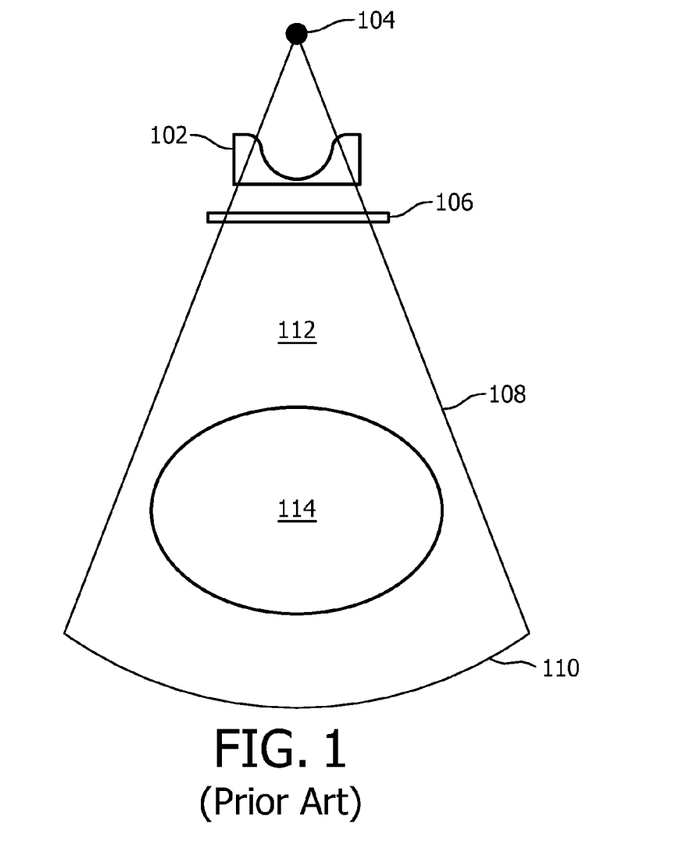
FIG. 1 schematically illustrates a prior approach to shaping a transmission profile of a radiation beam for a CT scanner.
Figure 2:
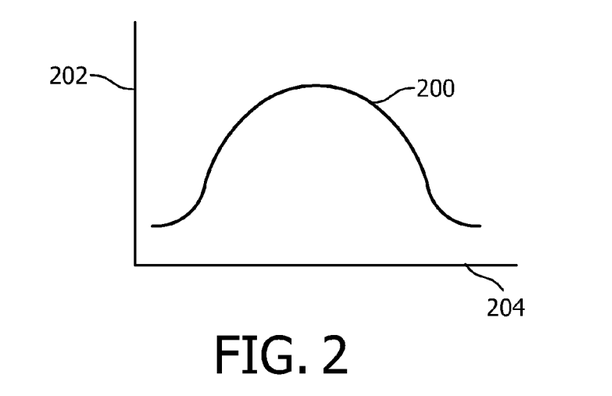
FIG. 2 illustrates an example shaped transmission profile using the prior art approach of FIG. 1.

A pre-patient radiation filter (often referred to as a bow-tie filter due to its shape) has been positioned between the focal spot and the collimator to spatially attenuate the emitted radiation to shape the transmission profile. FIG. 1 schematically illustrates an example of a bow-tie filter 102 in connection with a focal spot 104, a source collimator 106, an x-ray beam 108, a detector array 110, an examination region 112, and a portion of a subject or object 114 therein. Due to its shape, the bow-tie filter 102 heavily filters regions of the beam 108 that traverse only air, lightly filters the region of the beam 108 that traverses the subject 114, and varies the degree of filtering for the transitions there between. FIG. 2 illustrates an example resulting transmission profile 200 as a function of beam angle, where a y-axis 202 represents transmission and an x-axis 204 represents beam angle. Note that the profile 200 varies as a function of the thickness of filter 102.

Unfortunately, the bow-tie filter 102 also preferentially filters lower energy rays relative to higher energy rays, thereby changing the x-ray spectrum of the beam exiting the filter 102, relative to the beam entering the filter 102. This has been referred to as beam hardening. As such, the x-ray spectrum of the beam used to scan a subject or object may not be the optimal and/or the desired x-ray spectrum, which may degrade image quality. Additionally, the bow-tie filter 102 filter may produce undesired scatter, which may degrade image quality and increase patient dose. In view of at least the foregoing, there is an unresolved need for other configurations of beamshaping apparatuses.

Aspects described herein address the above-referenced problems and others.

In one aspect, an imaging system includes a radiation source that emits radiation that traverses in a direction of an examination region during a scan and a detector array located opposite the radiation source, across the examination region, which detects radiation traversing the examination region during the scan and produces a signal indicative thereof. A beamshaper, located between the radiation source and the examination region, defines a flux intensity profile of the radiation beam traversing the examination region. The beamshaper includes a plurality of x-ray attenuating elements, which attenuate x-rays incident thereon, interleaved with a plurality of material free regions, which pass x-ray unattenuated. A transmittance of the x-rays is greater nearer a center region of the beamshaper relative to ends regions of the beamshaper. A beamshaper mover translates the beamshaper during at least one acquisition interval of the scan.

In another aspect, a method emitting x-rays in a direction of an examination region during a scan. The method further includes filtering, with a beamshaper, the emitted beam to define an intensity profile of the radiation beam. The beamshaper includes a plurality of x-ray attenuating elements, which attenuate x-rays incident thereon, interleaved with a plurality of material free regions, which pass x-ray unattenuated. A transmittance of the x-rays is greater nearer a center region of the beamshaper relative to ends regions of the beamshaper. The method further includes translating the beamshaper during at least one acquisition interval of the scan. The method further includes detecting radiation traversing the examination region during the scan and producing a signal indicative thereof.

In another aspect, a method includes translating a beamshaper during at least one acquisition interval, which spread an attenuation of the beamshaper across the at least one acquisition interval, producing a uniform flux intensity profile across a detector array, relative to not translating the beamshaper.

The invention may take form in various components and arrangements of components, and in various steps and arrangements of steps. The drawings are only for purposes of illustrating the preferred embodiments and are not to be construed as limiting the invention.

Figure 3:
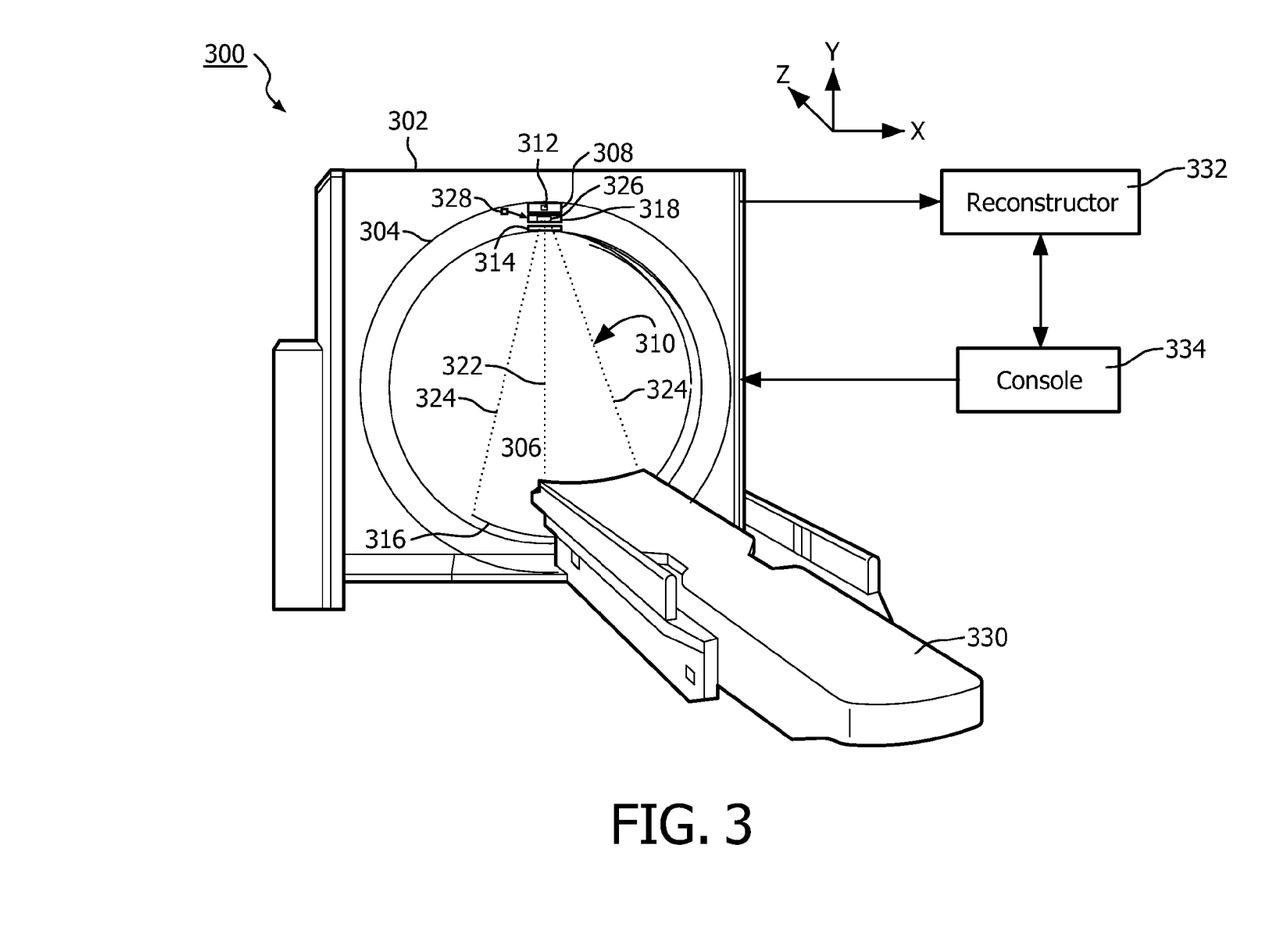
FIG. 3 schematically illustrates an example imaging system that includes a beamshaper and a beamshaper mover.

FIG. 3 illustrates an imaging system 300 such as a computed tomography (CT) scanner. The imaging system 300 includes a stationary gantry 302 and a rotating gantry 304, which is rotatably supported by the stationary gantry 302. The rotating gantry 304 rotates around an examination region 306 about a longitudinal or z-axis.

A radiation source 308, such as an x-ray tube, is supported by the rotating gantry 304 and rotates with the rotating gantry 304 about the examination region 306. The radiation source 308 emits radiation beam 310 from a focal spot 312 of an anode (not visible) of the source 308 essentially in all directions, including a direction of the examination region 306.

A source collimator 314 collimates the beam 310 to a pre-determined geometrical shape of interest, including a fan, a cone, a wedge, or other shaped beam 310 that traverses the examination region 306.

A radiation sensitive detector array 316 is located opposite the radiation source 308, across the examination region 306. The detector array 316 includes a one dimensional (1D) or two dimensional (2D) array of detector pixels that detect radiation traversing the examination region 306 and generate projection data indicative thereof.

A beamshaper 318 is arranged between the focal spot 312 and the examination region 306, for example, in the beam port of the source 308, which is located between the focal spot 312 and the collimator 314 and proximate to the focal spot 312, of a conventional CT scanner x-ray tube and/or elsewhere. The illustrated beamshaper 318 is configured to shape a transmission profile of the beam 310. This may include shaping the beam so that transmission is greater nearer a central ray 322 of the beam 310 and decreases in a direction away from the ray 322 and towards outer rays 324.

The transmission varies (linearly or non-linearly, in a deterministic or locally random but overall defined manner) in a single dimension, for example, along the x-direction, or in multiple dimensions, for example, in the x-z plane. In one instance, the beamshaper 318 includes a plurality of attenuating elements 326 interleaved with material free regions, in which the attenuating elements 326 fully or substantially attenuate rays incident thereon, and rays traversing paths through the material free regions traverse unattenuated. The beamshaper 318 can be used in place of or in combination with a conventional bow-tie filter like the bow-tie filter depicted in FIG. 1.

Figure 4:
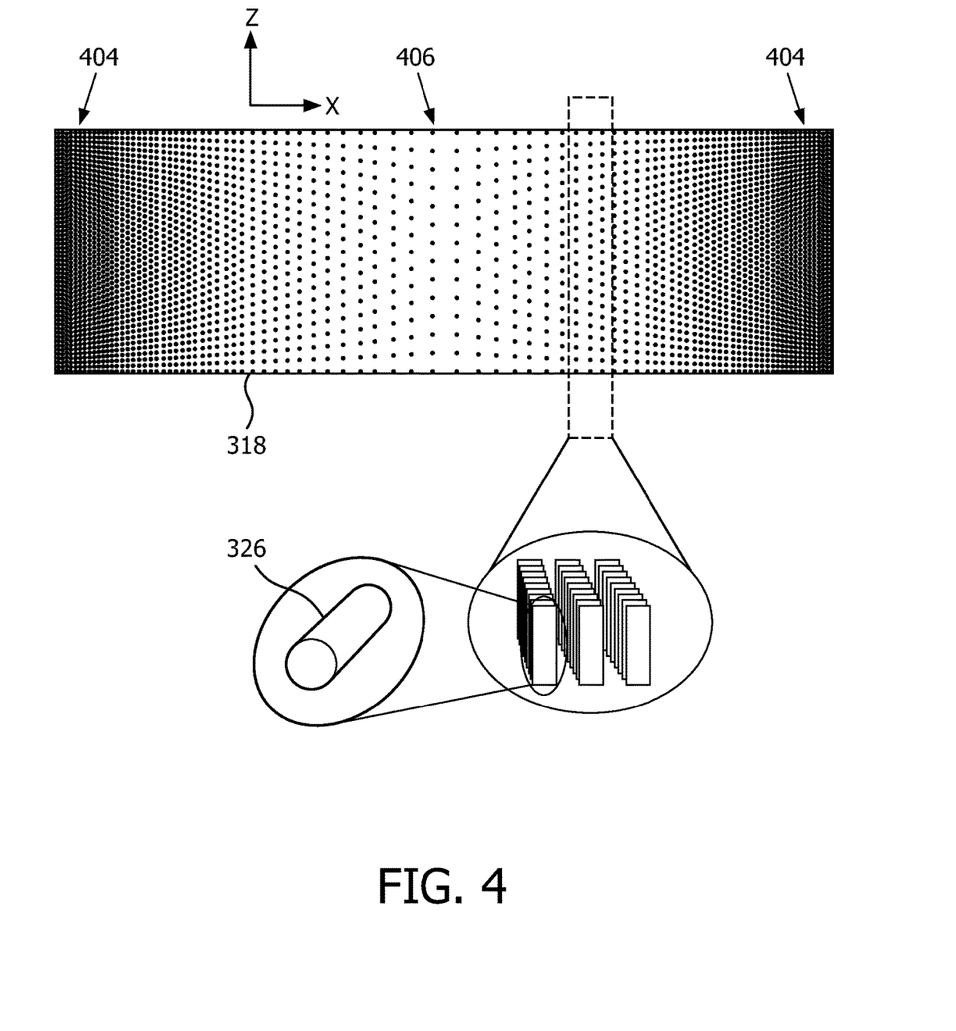
FIG. 4 schematically illustrates an example beamshaper.
Figure 5:
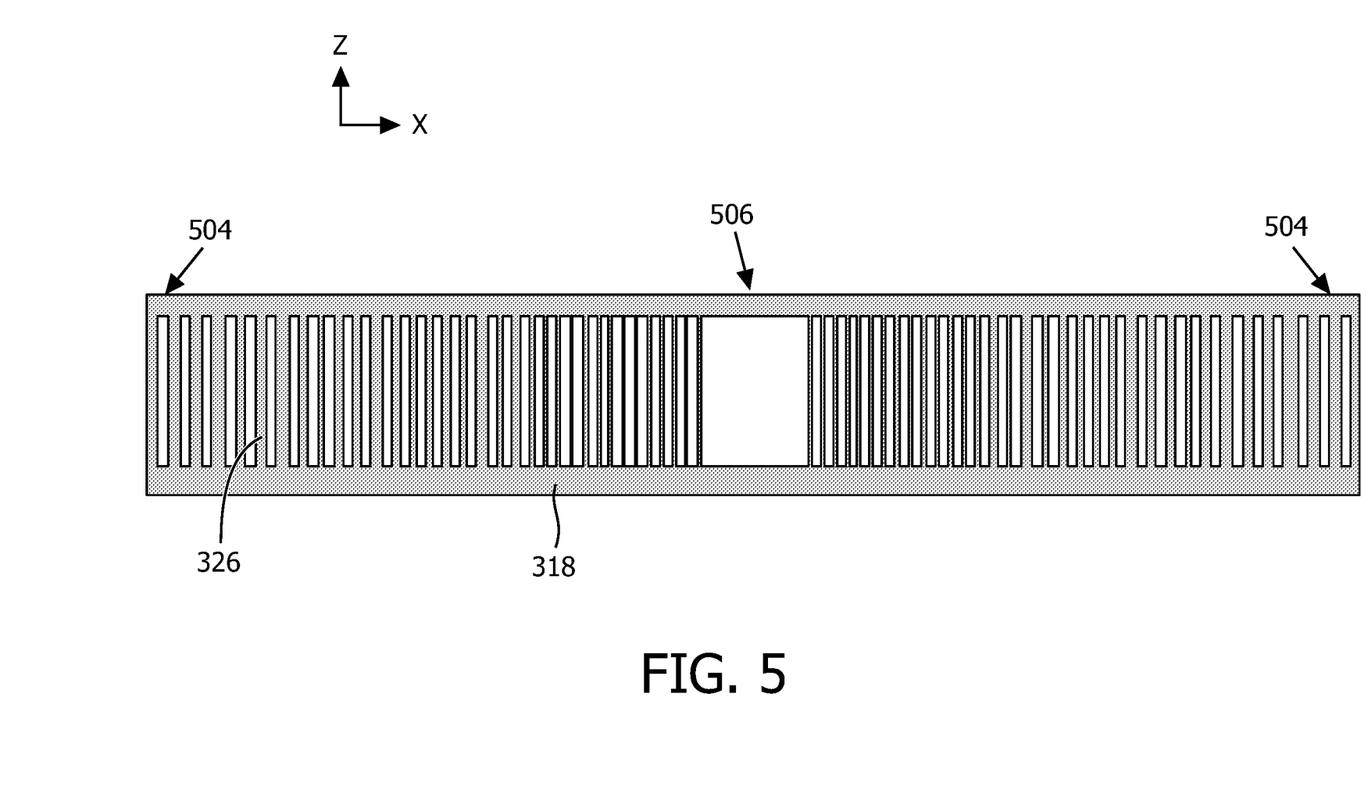
FIG. 5 schematically illustrates another example beamshaper.

FIGS. 4 and 5 show non-limiting examples of the beamshaper 318; it is to be understood that other configurations are also contemplated herein. FIGS. 4 and 5 both show a top down view, looking into the beamshaper 318 from the focal spot 312 in direction of the detector array 316.

In FIG. 4, the beamshaper 318 includes a two dimensional array of rod shape attenuating elements 326, which include a high Z material that fully or substantially fully attenuate x-rays incident thereon. The rod shape attenuating elements 326 are arranged so the outer regions 404 of the beamshaper 318 through which outer rays pass have a greater density of rods 326 relative to a central region 406 of the beamshaper 318 through which central rays pass.

As a result, the beamshaper 318 shapes the transmission profile of the emitted radiation so that transmission is greater nearer the central ray 322 (FIG. 3) of the beam and decreases in a direction away from the central ray and towards outer rays 324 (FIG. 3). This beamshaper is described in greater detail in International patent application serial number PCT PCT/IB2012/052814, filed on Jun. 5, 2012, entitled "X-Ray Beam Transmission Profile Shaper," and assigned to Koninklijke Philips Electronics N.V., which is incorporated by reference herein in its entirety.

In FIG. 5, the beamshaper 318 includes a 1D array of elongate strip shaped attenuating elements 326, which have a high Z material that fully or substantially fully attenuate x-rays incident thereon. The elongate strip shaped attenuating elements 326 are arranged parallel to each other along the z-axis with narrower gaps there between at the outer regions 504 through which outer rays pass with the gaps becoming wider approaching a central region 506 through which central rays pass.

As a result, the beamshaper 318 shapes the transmission profile of the emitted radiation so that transmission is greater nearer a central ray of the beam and decreases in a direction away from the central ray and towards outer rays. The beamshaper is described in greater detail in patent application Ser. No. 60/503,141, filed on Jun. 20, 2012, entitled "Radiation Beam intensity Profile Shaper," and assigned to Koninklijke Philips Electronics N.V., which is incorporated by reference herein in its entirety.

Other configurations of beamshapers are also contemplated herein, including, but not limited to, a combination of the beamshaper of FIG. 4 and the beamshaper of FIG. 5. This includes beamshapers with shapes other than rectangular. Another example of the beamshaper 318 is described in U.S. Pat. No. 4,672,648 to Mattson.

Returning to FIG. 3, a beamshaper mover 328 is configured to controllably dither the beamshaper 318. In one non-limiting instance, this includes translating the beamshaper 318 in at least the x-direction during an acquisition interval such that the attenuating elements 326 translate during the acquisition interval. The beamshaper 318 can additionally (concurrently or sequentially) or alternatively translate in the z-direction. In a variation, the beamshaper mover 328 controllably vibrates the beamshaper 318 to dither the beamshaper 318.

Figure 6:
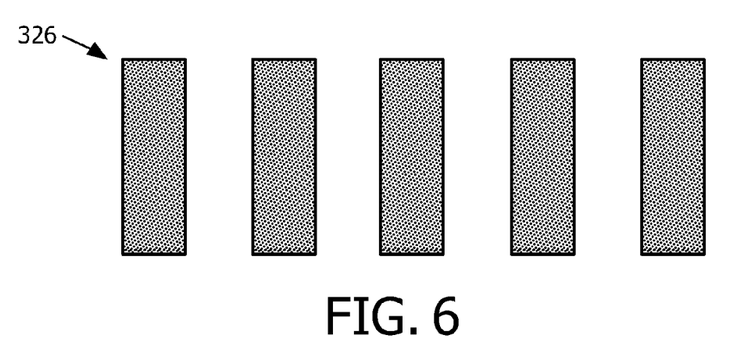
FIG. 6 schematically illustrates a translating beamshaper at a first location during an acquisition interval.
Figure 7:
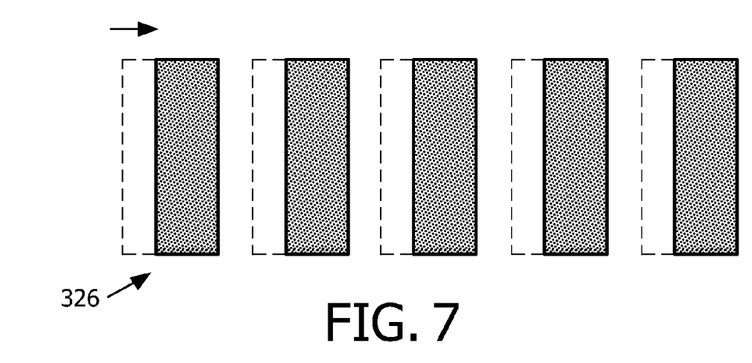
FIG. 7 schematically illustrates the translating beamshaper of FIG. 6 at a subsequent location during the acquisition interval.
Figure 8:
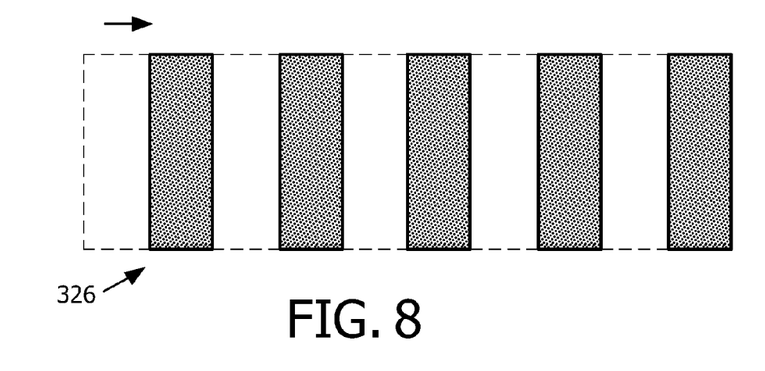
FIG. 8 schematically illustrates the translating beamshaper of FIG. 6 at a final location during the acquisition interval.

An example of the former, in connection with the beamshaper of FIG. 5, is shown in FIGS. 6, 7 and 8. FIG. 6 shows a set of the attenuating elements 326 at a first location at a beginning of an acquisition interval. In FIG. 7, the set of the attenuating elements 326 have translated approximately ¼ of a period, or a distance equal to approximately ½ of a width of one of the set of the attenuating elements 326. In FIG. 8, the set of the attenuating elements 326 have translated approximately ½ of a period, at the conclusion of the acquisition interval.

In FIGS. 6, 7, and 8, the attenuating elements 326 have equal width and equal spacing there between. In other embodiments, at least two of the attenuating elements 326 may have different widths and/or at least two pairs of the attenuating elements 326 may have different spacing there between. In addition, during an acquisition interval, at least one of the attenuating elements 326 may translate less than ½ of a period and/or at least one of the attenuating elements 326 may translate more than ½ of a period.

For instance, the attenuating elements 326 may translate with a frequency of one period per acquisition interval or multiple periods per interval, such as two, three, four, etc. periods per interval. Such translation may be created by moving the beamshaper 318 in only one direction during an acquisition (which may be the same direction or opposite direction of the previous and/or next acquisition interval) or moving the beamshaper 318 back and forth during at least one acquisition interval.

Figure 9:
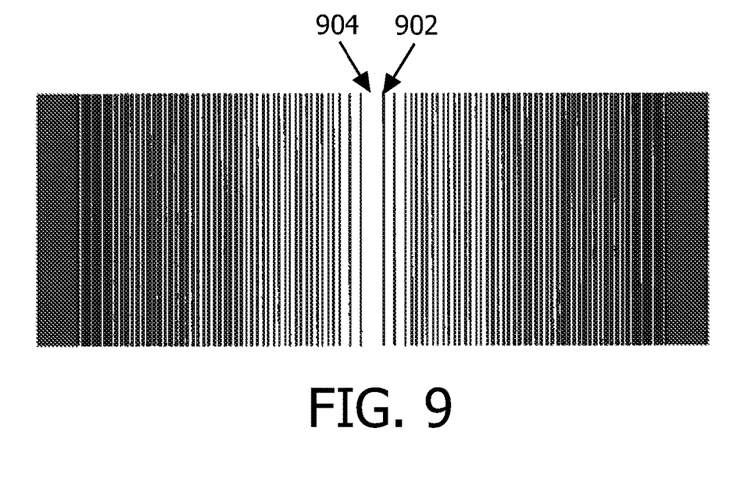
FIG. 9 illustrates an example flux profile for when the beamshaper is not translated.

Without such translating, for example, in connection with the beamshaper of FIG. 5, there would be alternating regions of no transmittance and full transmittance, which may result in a striped illumination intensity on the detector array 316. This is shown in a flux profile of FIG. 9, in which black regions 902 correspond to the attenuating elements 326 and the white regions 904 correspond to the gaps there between.

Figure 10:
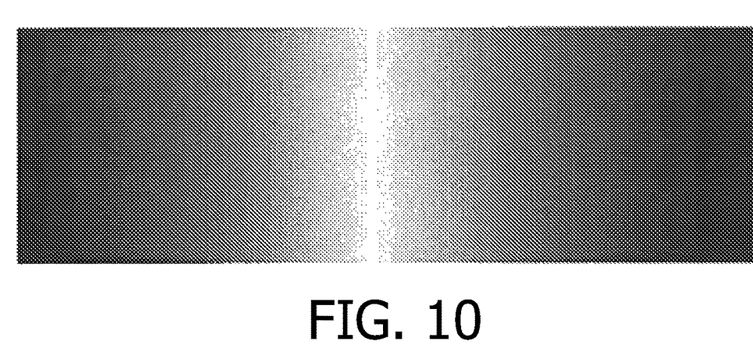
FIG. 10 illustrates an example flux profile for when the beamshaper is translated.

However, by translating the beamshaper 318 as described herein, the attenuating elements 326 are spread across the acquisition interval, mitigating the stripes, for example, by smoothing or blurring the attenuation. This is shown in the flux profile of FIG. 10, which, relative to the flux profile FIG. 9, has a smoother flux intensity across the detector array 316, as shown by the gray scale fluctuation. The translating may also reduce beam scatter and mitigate shading artifact, and facilitate countering the natural vibration of the system.

Returning to FIG. 3, a support 330, such as a couch, supports a subject in the examination region 306 and can be used to position the subject with respect to x, y, and/or z axes before, during and/or after scanning.

A reconstructor 332 reconstructs the projection data and generates three dimensional (3D) volumetric image data indicative of the examination region 306 and an object or subject therein. The resulting volumetric image data can be processed by an image processor or the like to generate one or more images.

A general purpose computing system serves as an operator console 334, and includes an output device such as a display and an input device such as a keyboard, mouse, and/or the like. Software resident on the console 334 allows the operator to control the operation of the system 300, for example, allowing the operator to initiate scanning, etc.

FIGS. 11, 12, 13, 14 and 15 show non-limiting examples of the beamshaper mover 328 in connection with the beamshaper 318. It is to be understood that the following are non-limiting and other configurations are contemplated herein.

Figure 11:
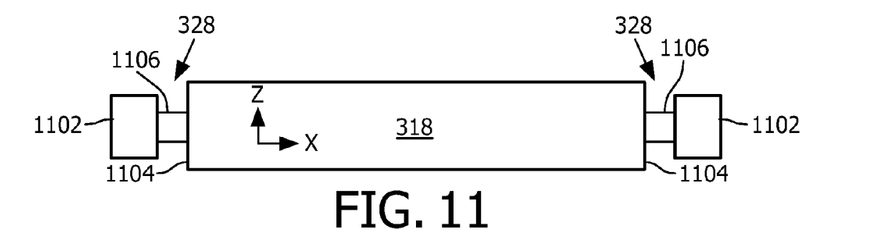
FIG. 11 schematically illustrates an example configuration of the beamshaper mover.

In FIG. 11, the beamshaper mover 328 includes motors 1102 at each end 1104 of the beamshaper 318. The motors 1102 include and drive shafts 1106 mechanically affixed to ends 1104 the beamshaper 318, which translates the beamshaper 318, in this instance, back and forth along the x-direction, as described herein. The illustrated motor 1102 is an ultrasonic piezoelectric motor. However, other motors are contemplated herein.

Figure 12:
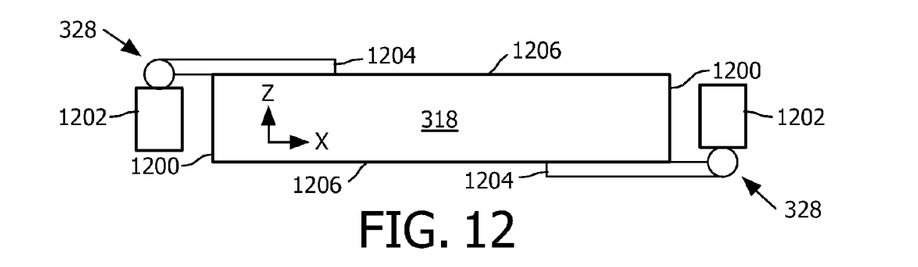
FIG. 12 schematically illustrates another example configuration of the beamshaper mover.

Likewise, in FIG. 12, the beamshaper mover 328 includes motors 1202 at each end 1200 of the beamshaper 318. The motors 1202 drive arms 1204 mechanically affixed to sides 1206 of the beamshaper 318, which translates the beamshaper 318 back and forth, in this instance, back and forth along the x-direction, as describe herein. The illustrated motor 1202 is a linear induction motor. However, other motors are contemplated herein such as high speed servos and/or other motors.

Figure 13:
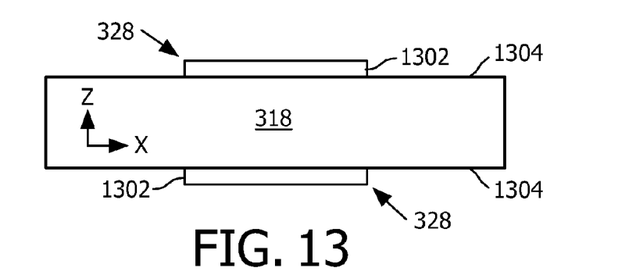
FIG. 13 schematically illustrates another example configuration of the beamshaper mover.

In FIG. 13, the beamshaper mover 328 includes piezoelectric or vibrating component 1302 at each side 1304 of the beamshaper 318. The piezoelectric component 1302 translates the beamshaper 318 by vibrating the beamshaper 318. In this example, the beamshaper translates in the z-direction, which is transverse to the translation direction of FIGS. 11 and 12.

Figure 14:
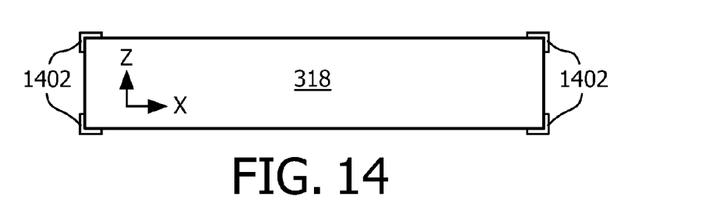
FIG. 14 schematically illustrates another example configuration of the beamshaper mover.

In FIG. 14, the beamshaper mover 328 includes brackets 1402 at the corners of the beamshaper 318. In this embodiment, the beamshaper mover 328 can be used to translate the beamshaper along the x/y-axis and/or the z-axis, concurrently and/or individually. The actuating mechanisms of FIGS. 11, 12, and/or 13, and/or other actuating mechanism can be used to move the brackets 1402.

Figure 15:
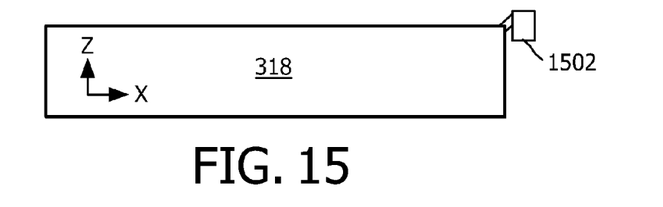
FIG. 15 schematically illustrates another example configuration of the beamshaper mover.

In FIG. 15, the beamshaper mover 328 includes a single component 1502 to translate the beamshaper 318, unlike in FIGS. 11-14 in which two or more components to translate the beamshaper 318.

It is to be understood that the example of FIGS. 11-15 are non-limiting and provide for explanatory purposes, and that other configurations are contemplated herein, including combinations of FIGS. 11-15 and/or other approaches.

For example, in FIGS. 11 and 12, two motors 1102 and 1202 are used in coordination to translate the beamshaper 318. However, in a variation, only a single motor 1102 and 1202 is used, and the other motor is replaced with a passive element (e.g. spring) that supports the translational movement. Similarly, In FIG. 13, one of the components 1302 can be replaced with a passive element that supports the translational movement. Furthermore, FIG. 15 shows only a single component 1502. However, in another embodiment, one or more supporting elements, located at the other end, one or more sides, one or more corners, etc. can be included.

In FIGS. 11-15, the beamshaper 318 is generally rectangular in shape. In other embodiments, the beamshaper 318 can be elliptical, circular, etc. shaped.

Figure 16:
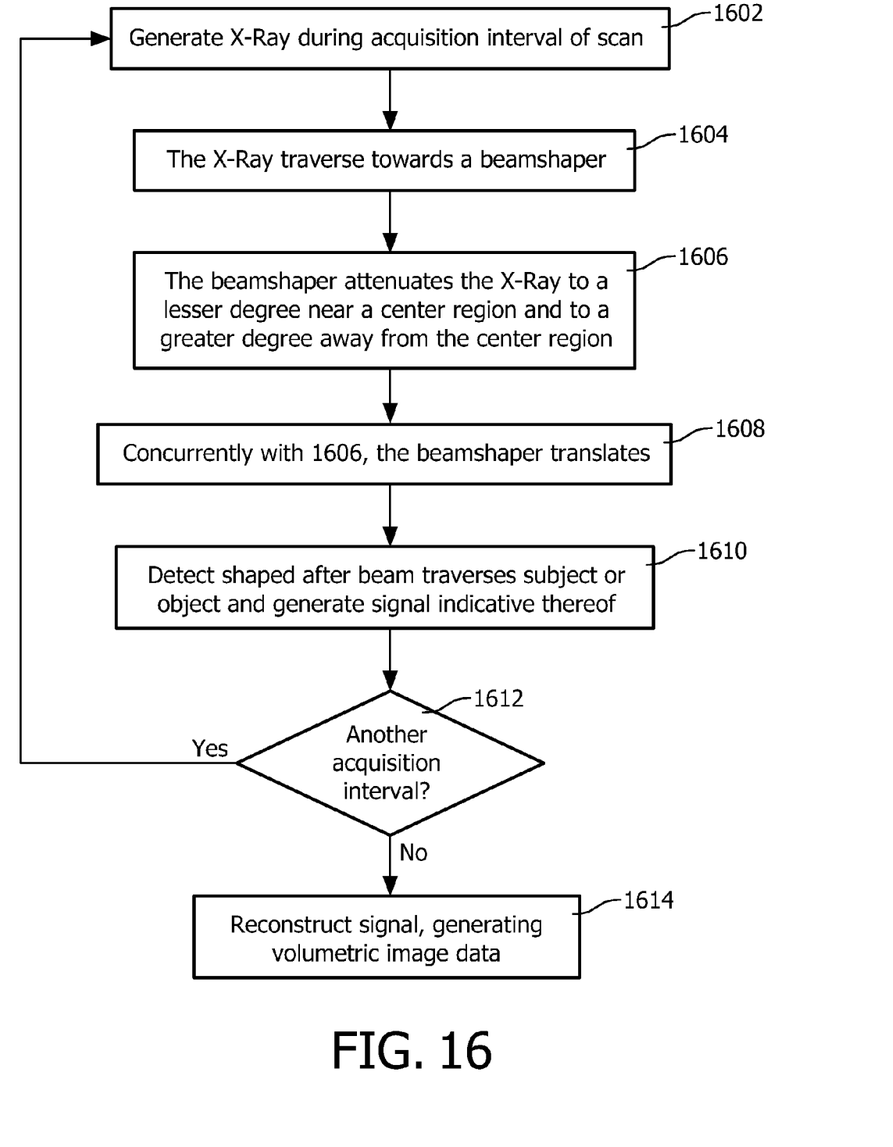
FIG. 16 illustrates an example method.

FIG. 16 illustrates an example method in accordance with the embodiments described herein.

It is to be appreciated that the ordering of the acts in the methods described herein is not limiting. As such, other orderings are contemplated herein. In addition, one or more acts may be omitted and/or one or more additional acts may be included.

At 1602, x-rays are generated during an acquisition interval of a scan.

At 1604, the x-rays traverses in a direction of a beamshaper.

At 1606, the beamshaper attenuates the x-rays traversing the beamshaper to a lesser degree near a center region and to a greater degree away from the center region.

As described herein, the beamshaper includes a plurality of attenuating elements and material free regions, in which the attenuating elements fully or substantially attenuate rays incident thereon, and rays traversing paths through the material free regions traverse unattenuated, and the attenuating elements are arranged to shape a transmission profile of the beam, for example, so that transmission is greater nearer a central ray of the beam and decreases in a direction away from the ray and towards outer rays.

At 1608, concurrently with act 1606, the beamshaper translates in the x/y and/or z-directions in at least one direction with a predetermined frequency.

As describe herein, this spreads the attenuation across an acquisition interval, which may mitigate stripes in the flux profile incident on the detector array, reduce beam scatter, and/or mitigate shading artifact.

At 1610, the beam exiting the beamshaper is collimated, traverses the examination region and a portion of a subject or object therein, and illuminates the detector array, which detects the incident beam and generates a signal indicative thereof.

At 1612, if the scan includes an additional acquisition interval, acts 1602 to 1610 are repeated.

Otherwise, at 1614 the signal is reconstructed, generating volumetric image data indicative of the scanned portion of the subject or object.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a radiation source configured to emit radiation that traverses in a direction of an examination region during a scan;
   a detector array located opposite the radiation source, across the examination region, configured to detect radiation traversing the examination region during the scan and produces a signal indicative thereof;
   a beamshaper, located between the radiation source and the examination region, configured to define a flux intensity profile of the radiation beam traversing the examination region,
   wherein the beamshaper includes a plurality of x-ray attenuating elements, configured to attenuate x-rays incident thereon, interleaved with a plurality of material free regions, which pass x-ray unattenuated,
   wherein the attenuating elements are arranged so that a density of the x-ray attenuating elements increases from a central region in a direction orthogonal to a direction of travel of the beam of radiation, wherein the central region has a non-zero density of attenuating elements; and
   wherein a transmittance of the x-rays is greater nearer a center region of the beamshaper relative to ends regions of the beamshaper; and
   a beamshaper mover configured to translate the beamshaper during at least one acquisition interval of the scan, wherein an acquisition interval occurs while the radiation source is emitting radiation and the detector array is receiving the emitted radiation.

2. The imaging system of claim 1, the beamshaper mover, comprising:
   at least one mover located at and affixed to at least one end of the beamshaper, wherein the mover configured to control the translation.

3. The imaging system of claim 1, the beamshaper mover, comprising:
   at least one mover located at least one end of the beamshaper and affixed to at least one side of the beamshaper, wherein the mover is configured to control the translation.

4. The imaging system of claim 1, the beamshaper mover, comprising:
   at least one mover located at least one side of the beamshaper, wherein the mover is configured to control the translation.

5. The imaging system of claim 1, wherein the beamshaper mover is configured to translate the beamshaper a distance approximately equal to a width of an attenuating element during the at least one acquisition interval.

6. The imaging system of claim 5, wherein the beamshaper mover is configured to translate the beamshaper in a single direction.

7. The imaging system of claim 5, wherein the beamshaper mover is configured to translate the beamshaper in more than one direction.

8. The imaging system of claim 7, wherein the beamshaper mover is configured to translate the beamshaper concurrently in more than one direction.

9. The imaging system of claim 1, wherein the beamshaper mover is configured to translate the beamshaper back and forth during the at least one acquisition interval at a predetermined frequency.

10. The imaging system of claim 1, wherein the attenuating elements are arranged in in a two dimensional array including a row of at least three attenuating elements and a column of at least three attenuating elements.

11. The imaging system of claim 1, wherein translating the beamshaper spreads the attenuation across the acquisition interval during the at least one acquisition interval.

12. The imaging system of claim 1, wherein translating the beamshaper is configured to reduce intensity fluctuations in a flux profile at the detector during the at least one acquisition interval.

13. The imaging system of any of claim 1, wherein translating the beamshaper is configured to mitigate shading artifact during the at least one acquisition interval.

14. A method, comprising:
   emitting x-rays in a direction of an examination region during a scan;
   filtering, with a beamshaper, the emitted beam to define an intensity profile of the radiation beam,
   wherein the beamshaper includes a plurality of x-ray attenuating elements, which attenuate x-rays incident thereon, interleaved with a plurality of material free regions, which pass x-ray unattenuated, and
   wherein the attenuating elements are arranged so that a density of the x-ray attenuating elements increases from a central region in a direction orthogonal to a direction of travel of the beam of radiation, wherein the central region has a non-zero density of attenuating elements;
   translating the beamshaper during at least one acquisition interval of the scan, wherein an acquisition interval occurs while x-rays are being emitted and the detector array is receiving the emitted radiation; and
   detecting radiation traversing the examination region during the scan and producing a signal indicative thereof.

15. The method of claim 14, wherein the attenuating elements are arranged in a two dimensional array including a row of at least three attenuating elements and a column of at least three attenuating elements.

16. The method of claim 14, further comprising:
   translating the beamshaper a distance approximately equal to at least a width of an attenuating element during an acquisition interval.

17. The method of claim 14, further comprising:
   translating the beamshaper in a single direction.

18. The method of claim 14, further comprising:
   translating the beamshaper concurrently in a more than one direction.

19. The method of claim 14, further comprising:
   wherein the attenuating elements are arranged in a matrix of at least three attenuating elements and in a column of at least three attenuating elements.

20. The imaging system of claim 1, wherein the attenuating elements are arranged in a matrix of at least three attenuating elements wide and in a column of at least three attenuating elements deep.

* * * * *